(12) United States Patent
Min et al.

(10) Patent No.: US 10,197,723 B2
(45) Date of Patent: Feb. 5, 2019

(54) OPTICAL FIBER, OPTICAL SENSOR INCLUDING OPTICAL FIBER, METHOD OF MANUFACTURING OPTICAL FIBER, AND DEPOSITION APPARATUS THEREFOR

(71) Applicant: INDUSTRY-ACADEMIC COOPERATION FOUNDATION, YONSEI UNIVERSITY, Seoul (KR)

(72) Inventors: Byung Kwon Min, Seoul (KR); Hang Eun Joe, Seoul (KR); Hye Bin Kim, Ansan-si (KR); Seung Yeon Nam, Incheon (KR); Jin A Bang, Daejeon (KR); Na Ha Chu, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 62 days.

(21) Appl. No.: 15/280,183

(22) Filed: Sep. 29, 2016

(65) Prior Publication Data
US 2017/0153388 A1   Jun. 1, 2017

(30) Foreign Application Priority Data

Dec. 1, 2015 (KR) .................. 10-2015-0170051

(51) Int. Cl.
*G02B 6/02* (2006.01)
*G02B 6/27* (2006.01)
(Continued)

(52) U.S. Cl.
CPC .......... *G02B 6/02309* (2013.01); *C03C 25/22* (2013.01); *C03C 25/46* (2013.01); *C03C 25/68* (2013.01); *G01D 5/35358* (2013.01); *G01N 21/553* (2013.01); *G01N 21/554* (2013.01); *G02B 6/02052* (2013.01); *G02B 6/2746* (2013.01); *G01N 21/7703* (2013.01); *G01N 2021/7736* (2013.01); *G01N 2201/088* (2013.01)

(58) Field of Classification Search
CPC .......................... G02B 6/29368; G02B 6/1226
See application file for complete search history.

(56) References Cited

FOREIGN PATENT DOCUMENTS

| CN | 102279438 A | * 12/2011 |
|---|---|---|
| JP | 2005049182 A | 2/2005 |

(Continued)

OTHER PUBLICATIONS

Communication dated Mar. 13, 2017 from the Korean Patent Office in counterpart application No. 10-2015-0170051.

*Primary Examiner* — Thanh Luu
(74) *Attorney, Agent, or Firm* — Sughrue Mion, PLLC

(57) ABSTRACT

Disclosed is an optical fiber including a plasmonic optical filter with a closed curved shape provided at, at least portion thereof. A method of manufacturing the plasmonic optical filter includes a step of exposing a core, a step of forming a thin metal film on the core through physical vapor deposition while rotating the core in a circumferential direction after changing a rotation axis of the core, and a step of patterning nanopatterns on the cylinder-shaped thin metal film using focused ion beam technique assisted with endpoint detection method. Due to such constitutions, an active area to generate an optical signal for optical sensor can be increased.

5 Claims, 15 Drawing Sheets

(51) Int. Cl.
*G01N 21/552* (2014.01)
*C03C 25/46* (2006.01)
*C03C 25/22* (2018.01)
*C03C 25/68* (2006.01)
*G01D 5/353* (2006.01)
*G01N 21/77* (2006.01)

(56) References Cited

FOREIGN PATENT DOCUMENTS

| | | |
|---|---|---|
| JP | 2011002423 A | 1/2011 |
| KR | 10-1136258 B1 | 4/2012 |
| KR | 1020130019889 A | 8/2013 |

\* cited by examiner

OPTICAL FIBER, OPTICAL SENSOR INCLUDING OPTICAL FIBER, METHOD OF MANUFACTURING OPTICAL FIBER, AND DEPOSITION APPARATUS THEREFOR

CROSS-REFERENCE TO RELATED APPLICATION

This application claims priority to and the benefit of Korean Patent Application No. 10-2015-0170051, filed on Dec. 1, 2015, the disclosure of which is incorporated herein by reference in its entirety.

BACKGROUND OF THE INVENTION

1. Field of the Invention

The present invention relates to an optical fiber, an optical sensor including optical fiber, a method of manufacturing the optical fiber, and a deposition apparatus for them, and more particularly to metallic structures on the side of an optical fiber for increasing an optical signal generation area, an optical sensor including optical fiber, a method of manufacturing the optical fiber, and a deposition apparatus for them.

2. Description of the Related Art

Recently, fiber-optic refractive index sensors utilizing surface plasmon resonance have been developed. Optical fibers have a superior electromagnetic interference shielding characteristic, fast response time, and ability to achieve long-distance transmission, but the sizes thereof are small. Accordingly, such optical fibers are used as platforms of biological/chemical sensors in various fields, e.g., microenvironments, such as blood vessels, carbon dioxide geologic storage facilities, and the like.

Meanwhile, existing refractive index sensors using the optical fibers have optical filter, which includes plasmonic structures, at end faces of the fibers. By the way, since an area of the optical filter is limited to a small area of the end face, a small amount of optical signals are disadvantageously generated. Accordingly, research into an optical fiber for increasing the amount of optical signals and a sensor using the optical fiber is underway.

Related Art Document

Patent Document (Patent Document 1) Korean Patent No. 10-1136258 (registration date: Apr. 5, 2012)

SUMMARY OF THE INVENTION

Therefore, the present invention has been made in view of the above problems, and it is an object of the present invention to provide an optical fiber including plasmonic optical filter for increasing an optical signal generation area, an optical sensor having the same, a method of manufacturing the optical fiber, and a deposition apparatus for them.

In accordance with the present invention, the above and other objects can be accomplished by the provision of an optical fiber, wherein a plasmonic optical filter having a closed curved shape is provided to at least a portion of the optical fiber.

According to an aspect, the plasmonic optical filter may be formed by patterning a thin metal film formed into a cylindrical shape at a portion of a circumferential surface of an exposed core with nanopatterns.

According to an aspect, the thin metal film may be made of at least one of gold, silver, aluminum, and chrome.

According to an aspect, the nanopatterns may include a plurality of holes perforating the thin metal film.

According to an aspect, the nanopatterns may be periodically arranged side by side.

In accordance with another aspect of the present invention, there is provided an optical sensor including: a core; a cladding surrounding a portion of the core and made of a material having a lower refractive index than a material of the core; and an optical filter formed into a cylindrical shape at another portion of the core and including a thin metal film patterned with nanopatterns.

In accordance with another aspect of the present invention, there is provided an optical sensor including: a light source for generating light; a probe for sensing the light guided to a target and transmitted, at least a portion of the probe including an optical fiber that includes a plasmonic optical filter having a closed curved shape; and a detector for detecting the target by detecting light transmitted from the probe.

According to an aspect, the optical sensor includes: input and sensing ports provided between the light source and probe and guiding input and sensing of the light; and a detection port provided between the probe and the detector and guiding detection of the light.

In accordance with another aspect of the present invention, there is provided an optical sensor, including: a light source for generating light; a probe for sensing the light guided to a target and being reflected, at least a portion of the probe including an optical fiber that includes a plasmonic optical filter having a closed curved shape; a detector for detecting the target by detecting the light reflected from the probe; and a circulator for circulating the light in an order of the light source, the probe, and the detector, the circulator being provided among the light source, the probe, and the detector.

According to an aspect, the optical sensor may include: an input port for guiding input of light, the input port being provided between the light source and the circulator; a sensing port for guiding sensing of light, the sensing port being provided between the probe and the circulator; and a detection port for guiding detection of light, the detection port being provided between the detector and the circulator.

In accordance with another aspect of the present invention, there is provided a method of manufacturing the optical fiber, the method including: exposing a core; forming a thin metal film on the core through physical vapor deposition, for example using an evaporator, while rotating the core in a circumferential direction; and patterning at least one nanopattern on the thin metal film to forming form a plasmonic optical filter.

According to an aspect, the exposing may include removing a cladding and a jacket surrounding an outer circumference of the core.

According to an aspect, the forming may include: inserting the core into a guider for changing a rotation axis of the core, inside a vacuum chamber; rotating the core in a circumferential direction in a state in which the guider is inserted into the guider; and physical-vapor-depositing the core, a metal source of which is exposed, in a cylindrical shape.

According to an aspect, the guider may be made of Teflon, includes a penetrated open window for exposing the core formed at a location facing the metal source, is curved to change a rotation axis of the core, and may have a hollow tube shape, wherein a diameter of the guider is greater than a diameter of the core.

According to an aspect, the open window may be coupled with a mask including at least one penetrated open hole through which the metal source passes.

According to an aspect, in the patterning, at least one nanopattern may include a plurality of perforated holes patterned side by side by machining the thin metal film by a focused ion beam system while detecting a real-time machined surface for machining endpoint detection.

In accordance with yet another aspect of the present invention, there is provided a deposition apparatus for manufacturing a plasmonic optical filter, including: a vacuum chamber; a guider which includes an open window formed at a portion of the guider and is provided inside the chamber, into which the optical fiber, a core of which is exposed by removing a cladding from the optical fiber, is inserted, and which is curved to change a rotation direction of the optical fiber; a driving unit for rotating the optical fiber, the driving unit being inserted into the guider; and a deposition unit for depositing a metal source on the core exposed through the open window.

According to an aspect, the guider may be made of Teflon and may have a hollow tube shape having a larger diameter than the optical fiber.

According to an aspect, the guider may include a curve unit curved into an L-shape such that the optical fiber is disposed at a location facing with the deposition unit, and has a hollow tube shape.

According to an aspect, the open window may be coupled with a mask that includes at least one penetrated open hole through which the metal source passes.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferred embodiments of the present disclosure are described with reference to the accompanying drawings.

Figure 1:
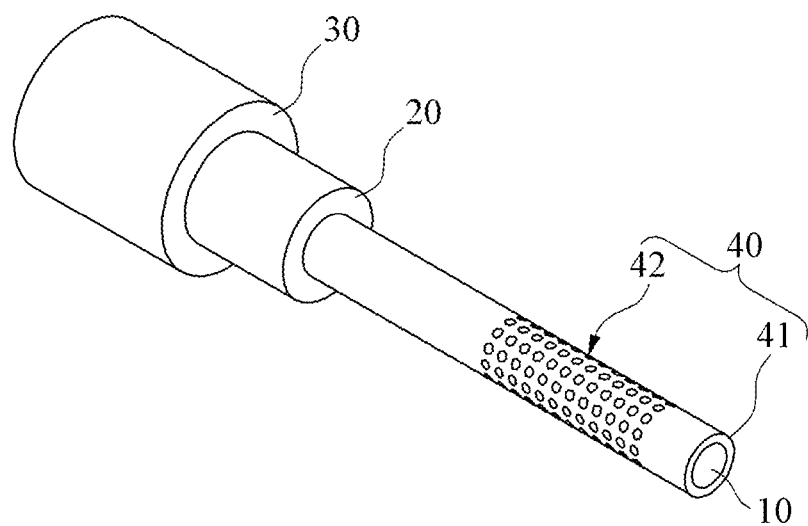
FIG. 1 is a perspective view schematically illustrating an optical fiber according to a preferred embodiment of the present disclosure.

Referring to FIG. 1, the optical fiber according to a preferred embodiment of the present disclosure 1 includes a cylindrical plasmonic optical filter 40 in at least a portion thereof. The optical fiber 1 may include a core 10, a cladding 20, a jacket 30, and a plasmonic optical filter 40.

The core 10 is disposed at the center of the optical fiber 1 may be made of a material having a relatively high refractive index, such as cylindrical silica.

The cladding 20 may surround a portion of the core 10, and may be made into a hollowed cylindrical shape such that the core 10 passes through the interior of the cladding 20. The cladding 20 may be made of a material, such as silica, having a smaller refractive index than the material of the core 10 such that light proceeding in the interior of the core 10 is totally reflected.

Although the optical fiber 1 according to the embodiment of the present disclosure includes both the core 10 and the cladding 20, the optical fiber 1 may include any one of the core 10 and the cladding 20, thus having a single refractive index. More particularly, when the optical fiber 1 has a single refractive index by including any one of the core 10 and the cladding 20, the optical fiber 1 may be formed into a structure in which a thin metal film is laminated on a fiber side of the core 10 or the cladding 20 having a single refractive index.

The jacket 30 may surround the cladding 20 and may protect the core 10 and the cladding 20 from external impact. The jacket 30 may be made of a synthetic resin coating material.

The optical filter 40 may be provided at a portion of the core 10, except for a portion surrounded by the cladding 20. The optical filter 40 may include a thin metal film 41, which is deposited on the core 10, and nanopatterns 42, which are formed by patterning the thin metal film 41. The nanopatterns 42 formed at the thin metal film 41 of the optical filter 40 may be nanoholes formed by perforating the thin metal film 41 at nanometer scale.

The thin metal film 41 may be made of at least one of gold, silver, aluminum, and chrome. The optical filter 40 may exhibit surface plasmon resonance effect, by which the optical filter 40 can filter specific-wavelength light out, due to the nanopatterns 42 formed at the thin metal film 41. The wavelengths of light may be varied depending upon the refractive indexes of medium near the optical filter 40. Accordingly, using such a phenomenon, change of medium near the optical filter 40 may be detected by monitoring wavelengths of the transmitted light.

In addition, surface plasmon resonance effect depends upon the arrangements and sizes of the nanopatterns 42 formed in the thin metal film 41. Further, the wavelengths of light filtered out at the optical filter 40 may be different depending upon the arrangements and sizes of the nanopatterns 42.

Figure 2:
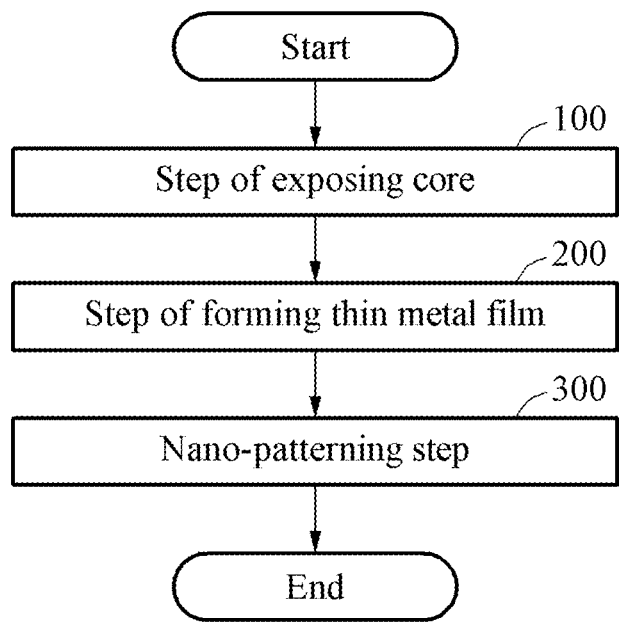
FIG. 2 is a flowchart schematically illustrating a method of manufacturing the optical fiber illustrated in FIG. 1.

A method of manufacturing the optical fiber 1 including the optical filter 40 includes a step of exposing the core 100, a step of forming a thin metal film 200, and the nanopatterning step 300, as illustrated in FIG. 2.

Hereinafter, the method of manufacturing the optical fiber 1 is sequentially described and the configuration of the optical fiber 1 is also described.

Figure 3:
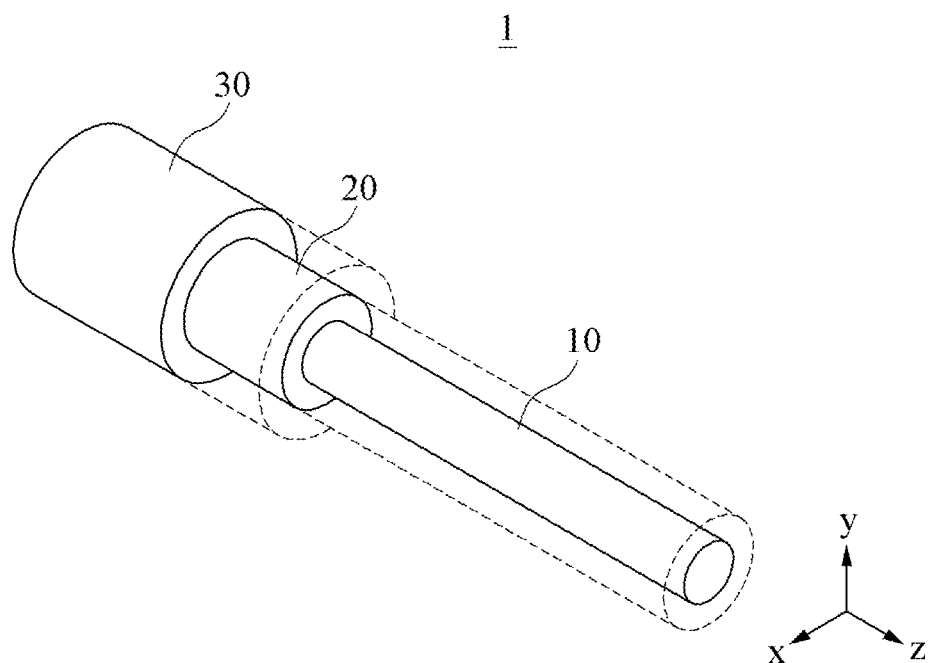
FIG. 3 is a perspective view schematically illustrating a core-exposed optical fiber to describe a step of exposing a core illustrated in FIG. 2.

In the step of exposing the core 100, the cladding 20 and the jacket 30 among the core 10, the cladding 20 and the jacket 30 constituting the optical fiber 1 are removed such that the core 10 is exposed, as illustrated in FIG. 3. Here, the jacket 30 may be physically, easily removed, whereas the cladding 20 may be removed by a special machining method, such as plasma etching or laser etching, or a chemical method, such as a wet etching method. In an embodiment of the present invention, the cladding 20 is removed using wet etching. However, when the optical fiber 1 includes any one of the core 10 and the cladding and thus has a single refractive index as described above, wet etching may be unnecessary.

The step of removing the cladding 20 by the wet etching method is described in detail. First, an optical fiber 1 including a step-index single-mode optical fiber or multi-mode optical fiber is prepared. Subsequently, a resultant optical fiber 1 or a plurality of resultant optical fibers 1 are immersed in an etching solution to be etched. Here, the ingredients of the core 10 and the cladding 20 of the optical fiber 1 are pure silica and F-doped silica, respectively. The etching solution includes hydrogen fluoride (HF) having high reactivity and thus allowing rapid etching of silica. An etched optical fiber 1 is washed with deionized water, although this is not illustrated in detail.

Figure 4:
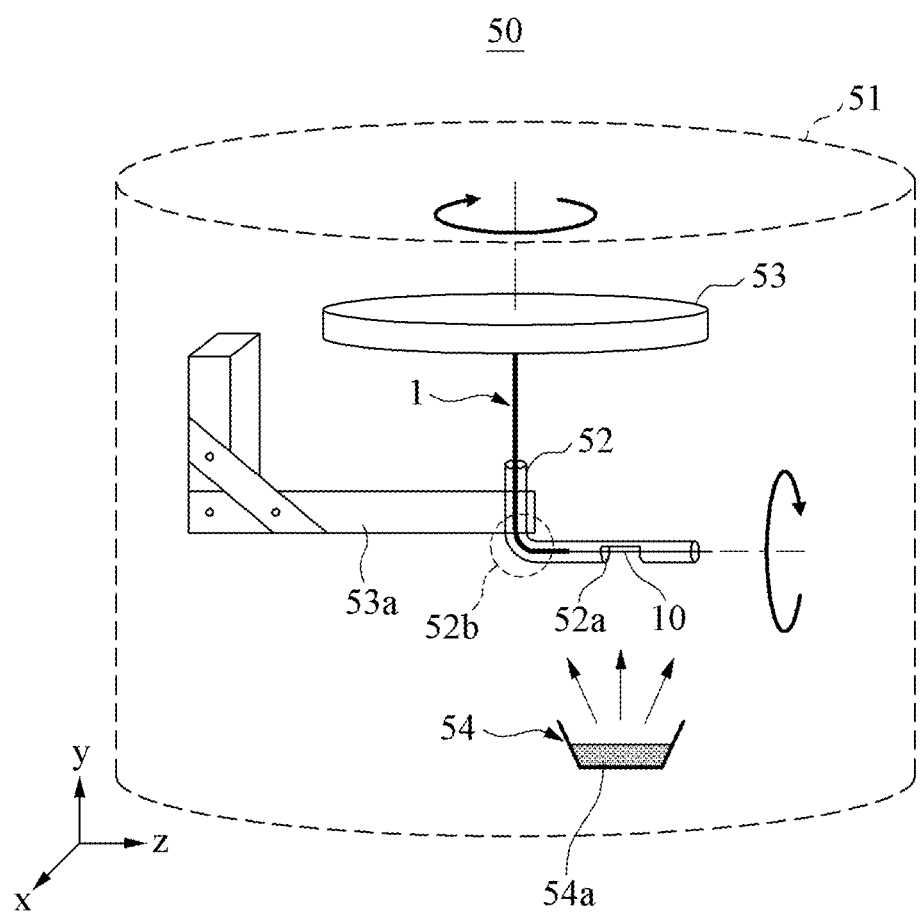
FIG. 4 schematically illustrates a deposition apparatus for manufacturing a plasmonic optical filter to describe a step of forming a thin metal film illustrated in FIG. 2.

In the step of forming a thin metal film 200, a closed cylindrical thin metal film 41 is formed on a circumferential surface of the core 10 exposed by shifting a rotation axis of the optical fiber 1 and rotating the shifted rotation axis. To accomplish this process, the physical vapor deposition apparatus, which is an evaporator in the present invention, 50 for manufacturing the optical filter 40 as illustrated in FIG. 4 is used in the step of forming a thin metal film 200.

The deposition apparatus 50 includes a vacuum chamber 51, a guider 52, the driving unit 53, and a deposition unit 54.

Since the interior of the chamber 51 is under vacuum, an environment in which the cylindrical thin metal film 41 is deposited by physical vapor deposition in a circumferential direction of the core 10 is provided.

The guider 52 is provided in the interior of the chamber 51. The guider 52 is manufactured into a hollow shape such that the optical fiber 1, from which the cladding 20 is removed to expose the core 10, can be inserted. In addition, the guider 52 includes an open window 52a, which is formed at a portion of the guider 52, and the curve unit 52b, which is curved to change a rotation direction of the optical fiber 1. The curve unit 52b of the guider 52 is provided to adjust a rotation axis of the optical fiber 1 having a flexible property. In an embodiment of the present invention, the rotation axis of the optical fiber 1 is changed to an angle of 90. That is, the guider 52 is curved in a direction facing the deposition unit 54 described below, thus guiding the optical fiber 1 to face the deposition unit 54.

For reference, the curve unit 52b is provided at a minimum to inhibit friction between the optical fiber 1 and the guider 52 which may occur during the rotation of the optical fiber 1. In an embodiment, the guider 52 of the present disclosure connects a rotation shaft of the driving unit 53, which is described below, to a side of the optical fiber 1 and includes a single curve unit 52b curved into an L-shape.

In addition, the guider 52 is made of Teflon having superior anti-chemical properties and heat resistance. Further, since the guider 52 is manufactured into a hollow shape while having a diameter larger than that of the optical fiber 1, friction between the guider 52 and the optical fiber 1 does not occur although the optical fiber 1 operates in the interior of the guider 52. For reference, when friction occurs between the guider 52 and the optical fiber 1, shearing modulus increases and, at the same time, torsional elastic energy increases, whereby energy transfer efficiency of the optical fiber 1 decreases.

The driving unit 53, which is included in commercial physical vapor deposition apparatuses (hereinafter referred to as a commercial apparatus, not shown), is used to improve the uniformity of a thin film by rotating a substrate, such as silicon substrate, in a circumferential direction. In the present disclosure, the aforementioned guider 52 is additionally installed at a commercial apparatus to transfer rotational force generated by the driving unit 53, which is included in the commercial apparatus, to the optical fiber 1.

When the optical fiber 1 is rotated by the driving unit 53 which is connected to a side of the optical fiber 1 inserted into the guider 52, the rotation is transferred to another end of the optical fiber 1 by the guider 52 which is curved at an angle of 90° and has the core 10. Accordingly, the other area of the optical fiber 1 inserted in the guider 52 rotates in a circumferential direction. For reference, although the optical fiber 1 in the interior of the guider 52 is rotated by the driving unit 53, the guider 52 is supported by the supporter 52a, thus being fixed in position.

With regard to the deposition unit 54, the core 10 exposed through the open window 52a of the guider 52 is deposited with a metal source 54a. The deposition unit 54 is disposed such that the optical fiber 1 inserted into the guider 52 is perpendicular to an evaporation direction of the metal source 54a, and thus, the optical fiber 1 is deposited with the thin metal film 41. Here, the thin metal film 41 deposited through the deposition unit 54 is formed of the metal source 54a including at least one of gold, silver, aluminum, and chrome.

Figure 5:
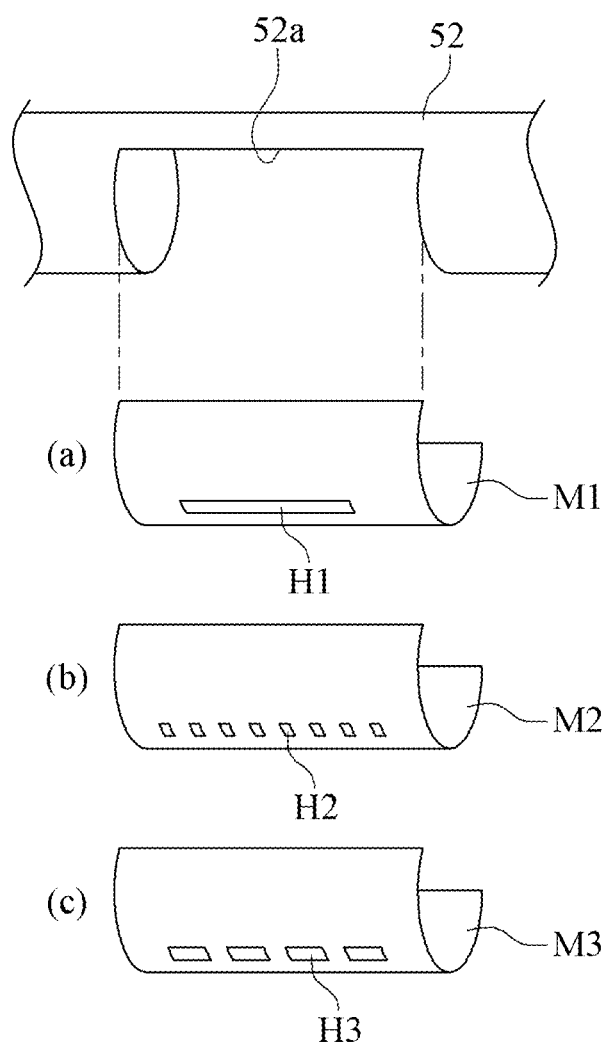
FIG. 5 schematically illustrates examples of a mask that may be installed at an open window of a guider illustrated in FIG. 4.

Referring to FIG. 5, examples of a mask, M1, M2, and M3, which are installed at the open window 52a of the guider 52 and may be coupled with the guider 52, are schematically illustrated. As illustrated in FIG. 5, each of the masks M1, M2, and M3 that may be installed at the open window 52a includes at least one open hole of H1, H2, and H3 having different shapes. That is, the masks M1, M2, and M3 illustrated in FIGS. 5(a), (b), and (c) have different widths and at least one of perforated open holes, H1, H2, and H3. The shapes, sizes, and numbers of the open holes, H1, H2, and H3, are not limited to the embodiments illustrated in (a), (b) and (c) of FIG. 5. Due to the masks M1, M2, and M3 with various open hole shapes, H1, H2, and H3, installed at the open window 52a, the thin metal film 41 may be laminated on the core 10 in various shapes.

Figure 6A:
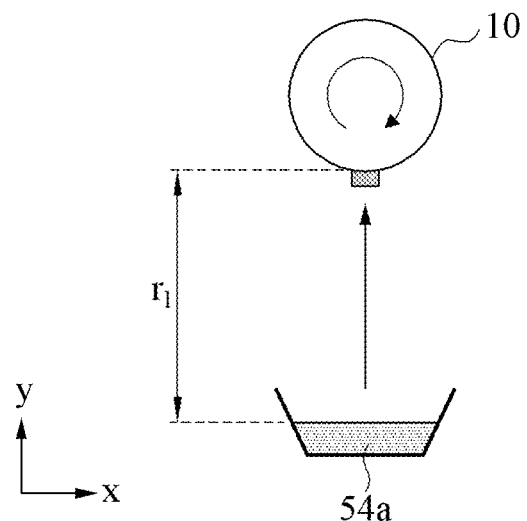
FIGS. 6A and 6B illustrate a spacing distance between a core and a metal source from different directions.
Figure 6B:
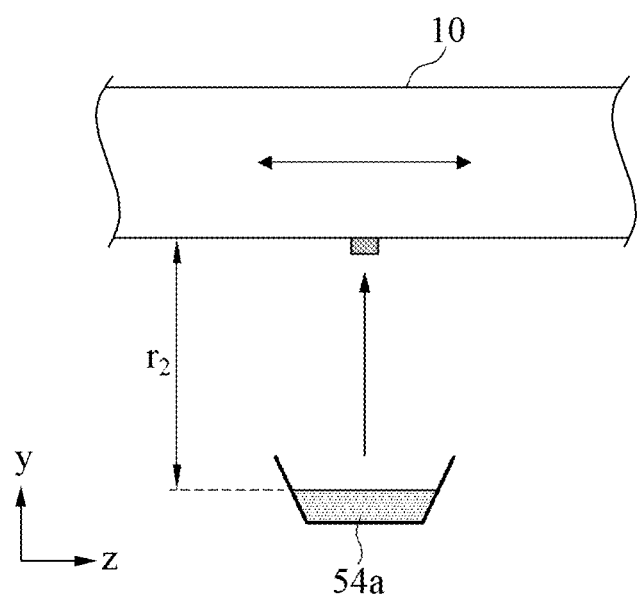

Meanwhile, as illustrated in FIG. 6A, the exposed core 10 of the optical fiber 1 is disposed in a perpendicular direction to an evaporation direction of the metal source 54a, and thus, the cylindrical thin metal film 41 is deposited when the core 10 is rotated in a circumferential direction. Meanwhile, as illustrated in FIG. 6B, rectilinear motion of the optical fiber 1 may occur by runout due to a difference in diameter between the optical fiber 1 and the guider 52. As illustrated in FIGS. 6A and 6B, the rotational and rectilinear motions of the optical fiber 1 allow distances r1 and r2 between the core 10 and the metal source 54a to be maintained while the thin metal film 41 is vapor-deposited along the circumference of the core 10.

For reference, to uniformly laminate the thin metal film 41 on the core 10 using vacuum vapor deposition, a deposition speed of the metal source 54a should be kept constant. Here, the deposition speed of the metal source 54a is determined by a deposition location determined by the angle (θ, Φ) of the center of a side of each of the metal source 54a and the base substrate, the core 10, and distances r1 and r2 according to the Langmuir-Knudsen equation disclosed in Equation 1 below:

$$R_m = C(M/T)^{0.5} \cos\theta \cos\phi 1/r^2 (P_e - P)$$ [Equation 1]

Figure 7:
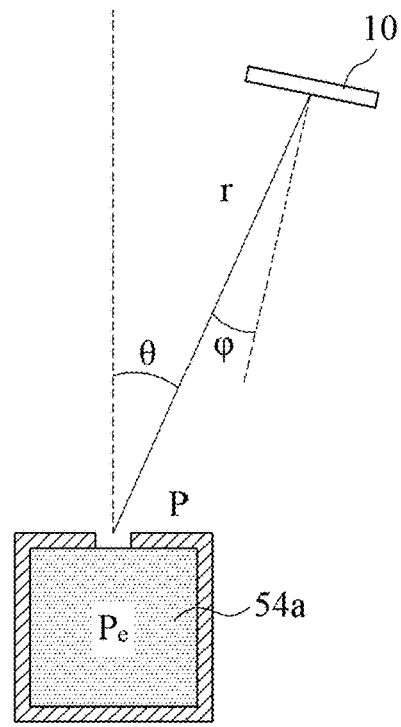
FIG. 7 is a schematic view to describe Langmuir-Knudsen equation.

In the equation, C represents a constant value of $1.85 \times 10^{-2}$, M represents molecular weight, r(cm) represents a distance between the metal source 54a and the core 10, T(k) represents the temperature of the metal source 54a, $P_e$ (torr) represents a steam pressure as a function of T, and P represents the pressure of the chamber 51 (see FIG. 7). For reference, P becomes 0 under high vacuum.

Figure 8:
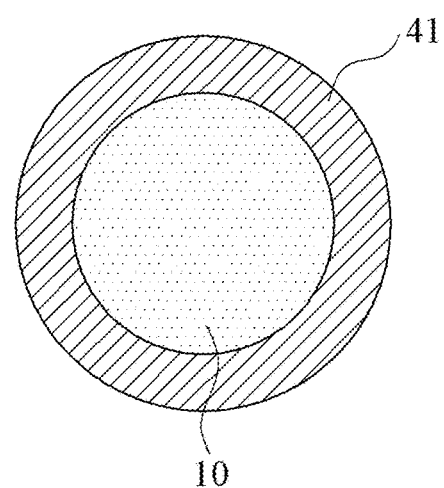
FIG. 8 is a sectional view schematically illustrating a state in which a cylindrical thin metal film is uniformly formed in a circumferential direction of a core.
Figure 9A:
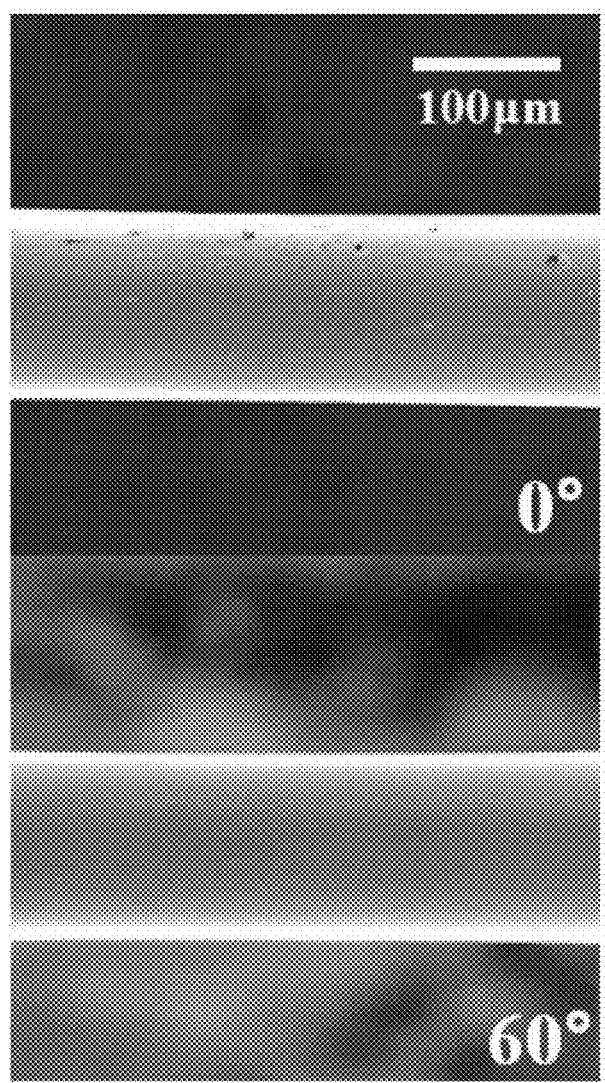
FIGS. 9A and 9B schematically illustrate images of cylindrical thin metal films deposited on cores.
Figure 9B:
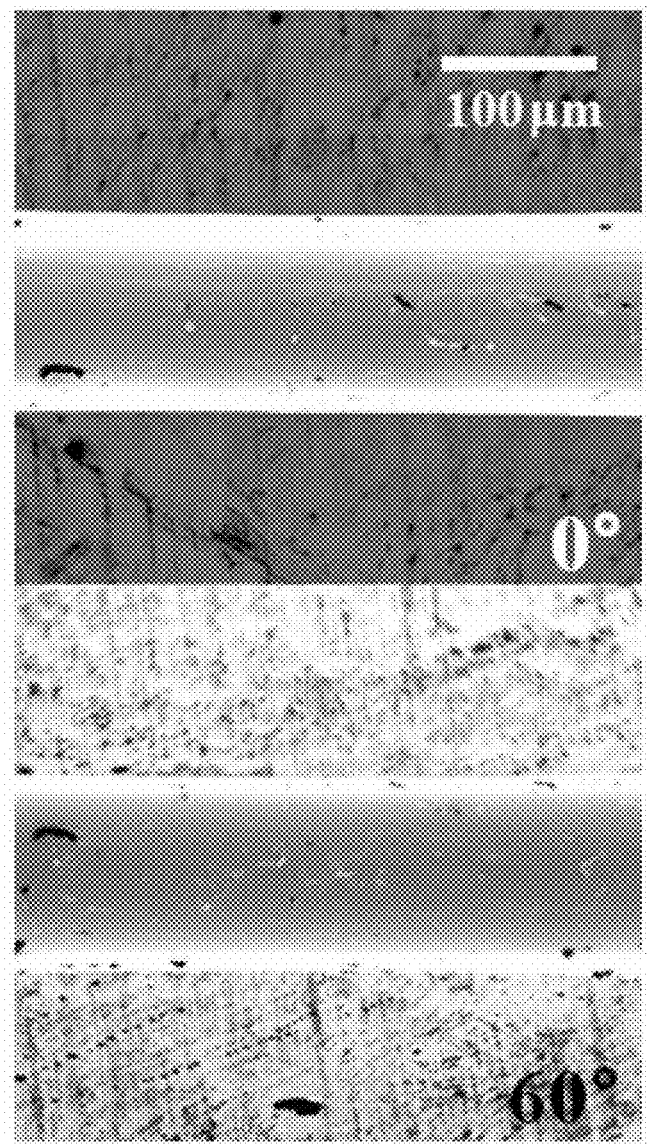

The thin metal film 41 deposited on the exposed core 10 of the optical fiber 1 by means of the deposition apparatus 50 is uniformly formed as a closed curved surface, i.e., into a cylindrical shape, along the circumference of the core 10, as illustrated in FIG. 8. FIGS. 9A and 9B illustrate images of aluminum thin films uniformly laminated to a thickness of 100 nm on the core 10 of the optical fiber 1.

Figure 10:
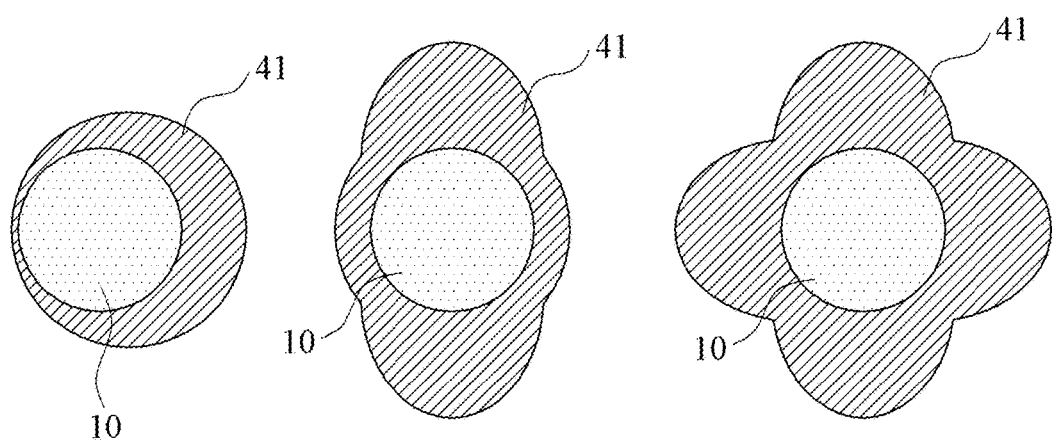
FIG. 10 schematically illustrates various deposition shapes of a thin metal film due to control of the rotation speed of a core.

Meanwhile, as illustrated in FIG. 10, the cylindrical thin metal film 41 may be formed into various shapes along the circumferential direction of the core 10 of the optical fiber 1 by changing the rotation speed of the optical fiber 1. For reference, since the characteristics of transmitted light depend upon the shapes of the thin metal film 41, the thin metal film 41 may be utilized as a platform for various plasmonic optical filters 40.

When the thin metal film 41 is formed, the nanopatterns 42 are formed at the cylindrical thin metal film 41 (step 300). In the patterning step (step 300), the core 10 is machined using a focused ion beam (I) assisted with a machining endpoint detection method investigating a real-time machined surface 41, thereby patterning the nanopatterns 42 including a plurality of holes. However, the method of forming holes in the thin metal film 41 is not limited to the machining endpoint detection method and any method of forming nanoscale holes at the thin metal film 41 may be used.

In particular, machined depths may be different upon machining with focused ion beam (I) since a surface of the cylindrical thin metal film 41 formed on the core 10 is curved, and thus, the machining endpoint detection method is used. Upon machining with the focused ion beam (I) assisted with the machining endpoint detection method, a time point at which a material of a machined surface is changed as illustrated in FIG. 11 is detected as a machining endpoint using SE images of a machined surface of the thin metal film 41 measured in real-time.

Figure 11:
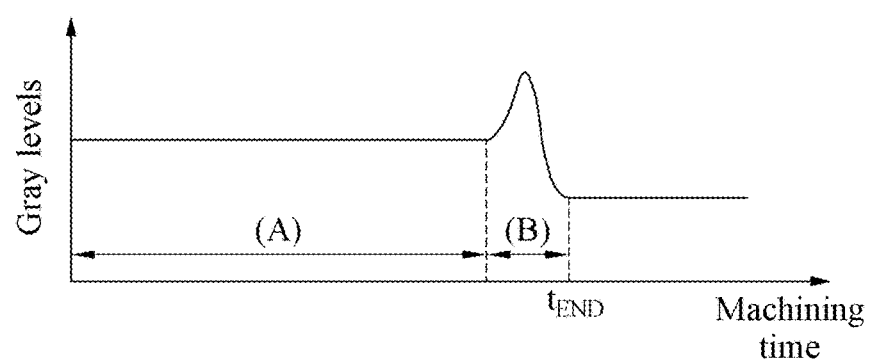
FIG. 11 is a graph schematically illustrating gray levels of secondary electron images that are monitored while focused ion beam machining in order to detect machining endpoint.

A time point at which the machined surface, i.e., the surface material of the thin metal film 41, is changed, may be detected by monitoring the gray level of an SE image as illustrated in FIG. 11. Here, as illustrated in FIG. 11, a time point at which a graph is kept constant after a temporal change of the graph corresponds to a machining endpoint ($t_{END}$) at which a material of the thin metal film 41 is completely changed.

Figure 12:
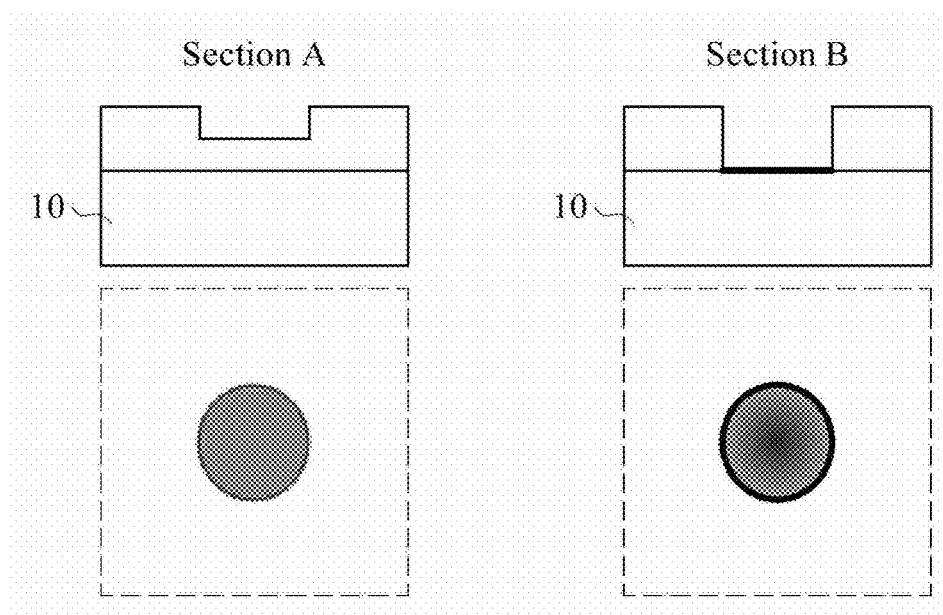
FIG. 12 schematically illustrates focused ion beam machining statuses in the (A) and (B) sections of the gray level graph illustrated in FIG. 11.
Figure 13A:
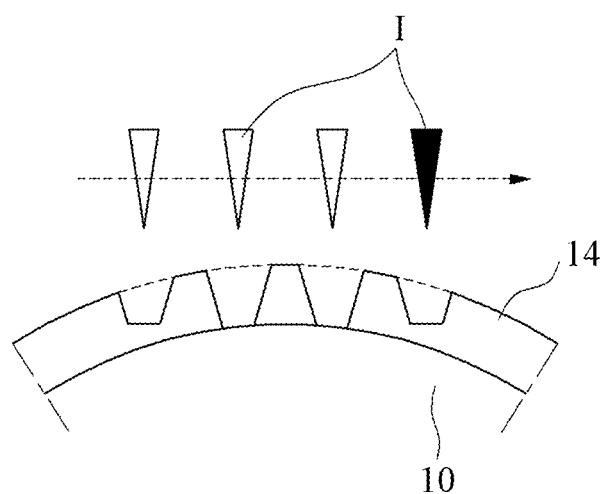
FIGS. 13A and 13B schematically compare machining error occurring when nano-patterning is performed on a thin metal film deposited at a side of a core with a precisely machined state using machining endpoint detection.
Figure 13B:
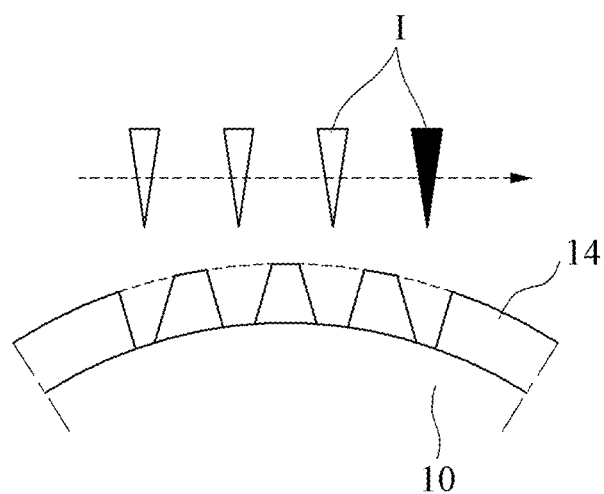

For reference, FIG. 12 illustrates focused ion beam machining states in sections (A) and (B) of the gray level graph illustrated in FIG. 11. In addition, FIGS. 13A and 13B illustrate states in which a machining error occurs upon nano-patterning of the thin metal film 41 deposited at a side of the core, and a precisely machined state using the machining endpoint detection method. As such, the precision of nano-patterning of the cylindrical thin metal film 41, i.e., the thin metal film 41 formed in a cylindrical shape, formed on the core 10 is improved through machining endpoint detection.

In an embodiment of the present invention, the nanopatterns 42, which are machined using focused ion beam (I) equipment using the machining endpoint detection method, is arranged into a bowie-shaped holes array having a size of about 0.7 μm*1.16 μm, although not described in detail.

Figure 14A:
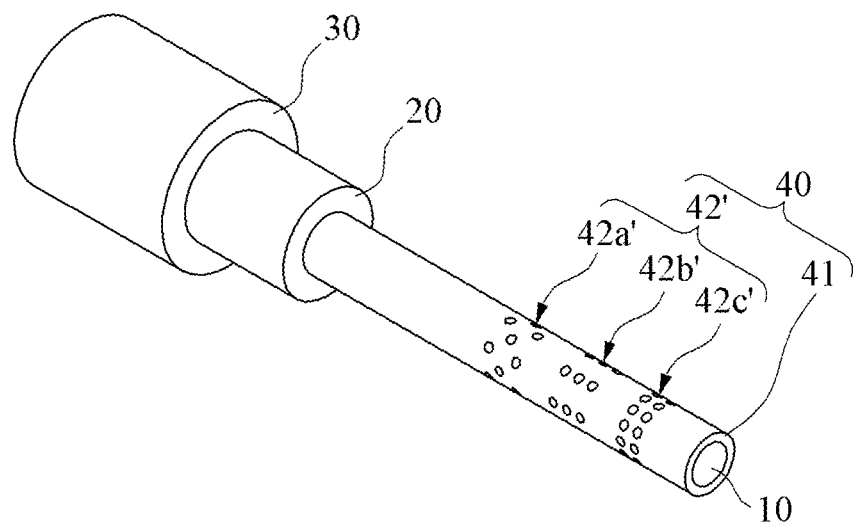
FIGS. 14A and 14B schematically illustrate an embodiment of a plasmonic optical filter including a plurality of nanopatterns with various shapes and a light transmission spectrum obtained due to the nanopatterns.
Figure 14B:
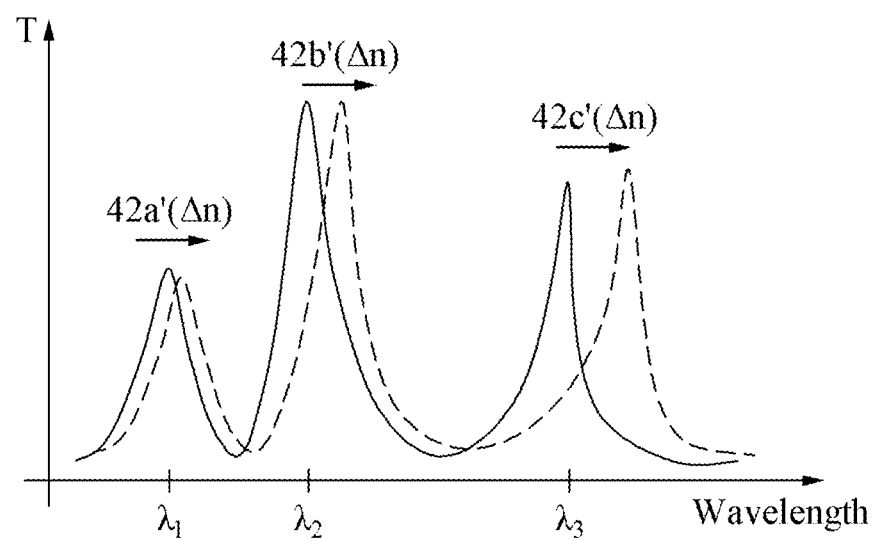

Referring to FIGS. 14A and 14B, another embodiment of nanopatterns 42' is illustrated. The nanopatterns 42' illustrated in FIG. 14A include the first to third patterns 42a', 42b', and 42c' which are provided at the thin metal film 41, have different pattern shapes, are spaced from each other, and are arranged side by side. That is, the nanopatterns 42' include a plurality of nanopatterns, i.e., the first to third patterns, 42a', 42b', and 42c', including a plurality of holes formed into different patterns. With regard to optical signals generated by the optical fiber 1 that includes the nanopatterns 42' including the first to third patterns, 42a', 42b', and 42c', as illustrated in FIG. 14B, the first to third patterns 42a', 42b', and 42c' exhibit different plasmon resonance frequencies ($\lambda_1$, $\lambda_2$, and $\lambda_3$), respectively.

Here, the sensitivities of resonance frequencies ($\lambda_1$, $\lambda_2$, and $\lambda_3$) of the nanopatterns 42' including the first to third patterns 42a', 42b', and 42c' differ depending upon refractive index changes (Δn) in ambient media. For example, a change in the refractive index gradually increases in an order of the first pattern 42a', the second pattern 42b', and the third pattern 43c'. Accordingly, the nanopatterns 42' including the first to third patterns 42a', 42b', and 42c' may provide improved measurement precision compared to the single-shaped nanopatterns 42 illustrated in FIG. 1 and, at the same time, is advantageous in measuring various materials.

Light transmission quality of the optical fiber 1 including the plasmonic optical filter 40 manufactured as described above is compared to a conventional optical fiber as illustrated in FIGS. 15A, 15B, 16A and 16B.

Figure 15A:
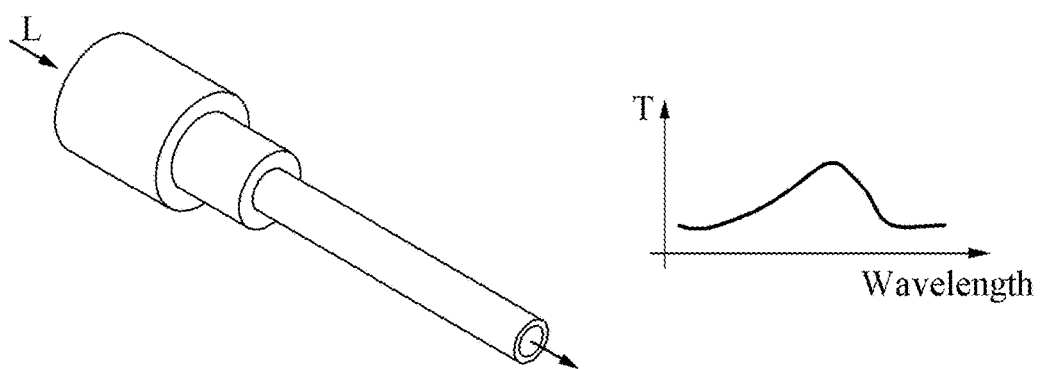
FIGS. 15A and 15B schematically compare light transmission states of an optical fiber with a thin metal film only and an optical fiber according to the present disclosure.
Figure 15B:
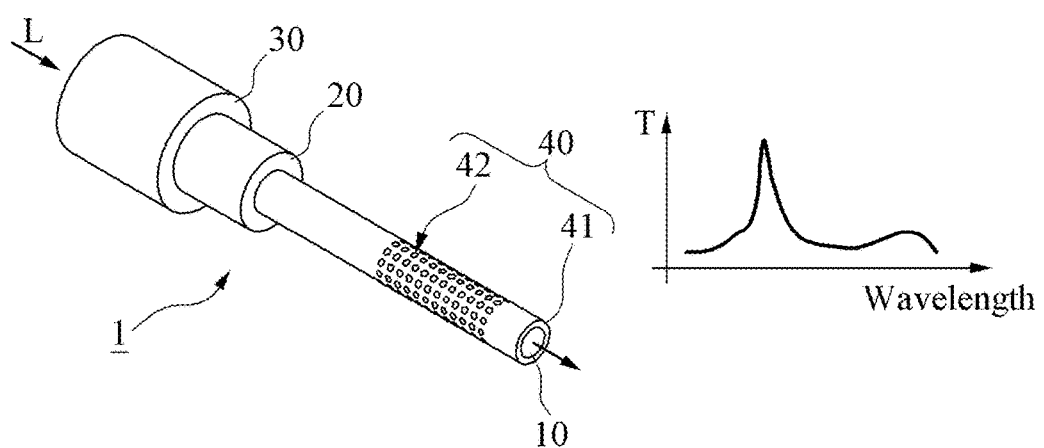

FIG. 15A illustrates the spectrum of light transmitted through a conventional optical fiber not including the optical filter 40. FIG. 15B illustrates the spectrum of light transmitted through the optical fiber 1 including the optical filter 40 according to the present disclosure. As illustrated in FIGS. 15A and 15B, the optical fiber 1 including the plasmonic optical filter 40 exhibits a superior spectrum result of the transmitted light.

Figure 16A:
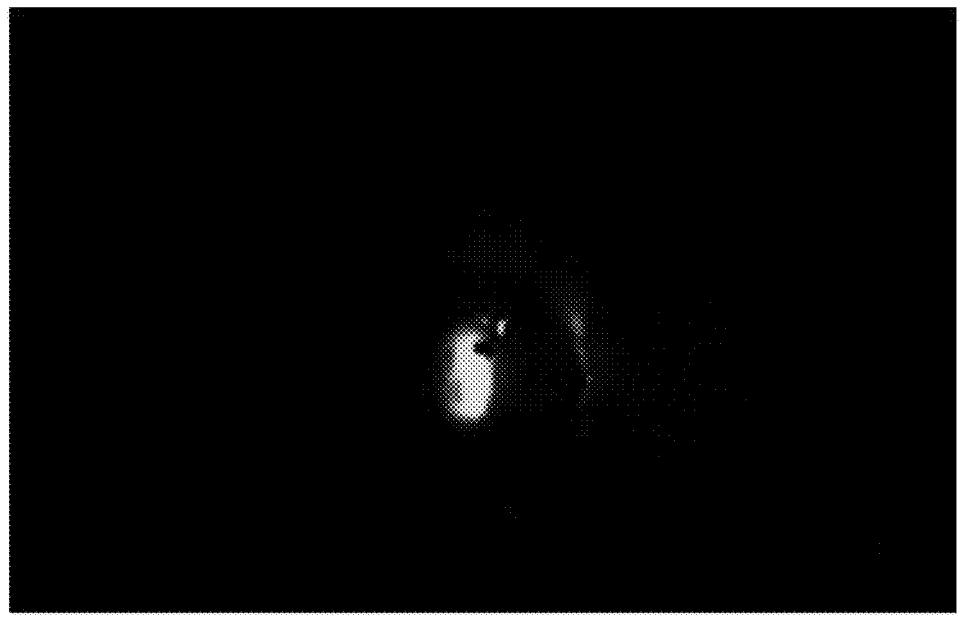
FIG. 16A illustrates an image of a light transmission state using an optical fiber with a thin metal film only.
Figure 16B:
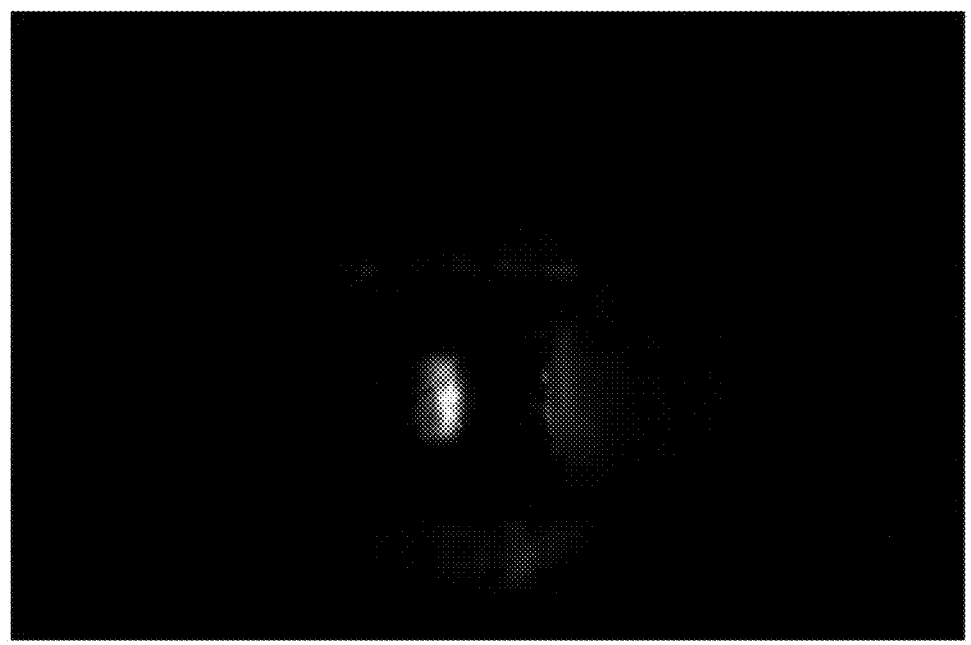
FIG. 16B illustrates an image of a light transmission state using an optical fiber according to the present disclosure.

In addition, FIG. 16A illustrates a state of light transmitted through the conventional optical fiber not including the optical filter 40, and FIG. 16B illustrates a state of light transmitted through the optical fiber 1 including the plasmonic optical filter 40 according to the present disclosure. In FIG. 16A, when white light is transmitted, yellow light is transmitted. On the other hand, in FIG. 16B, by using the plasmonic optical filter 40, white light is filtered into green light.

Figure 17:
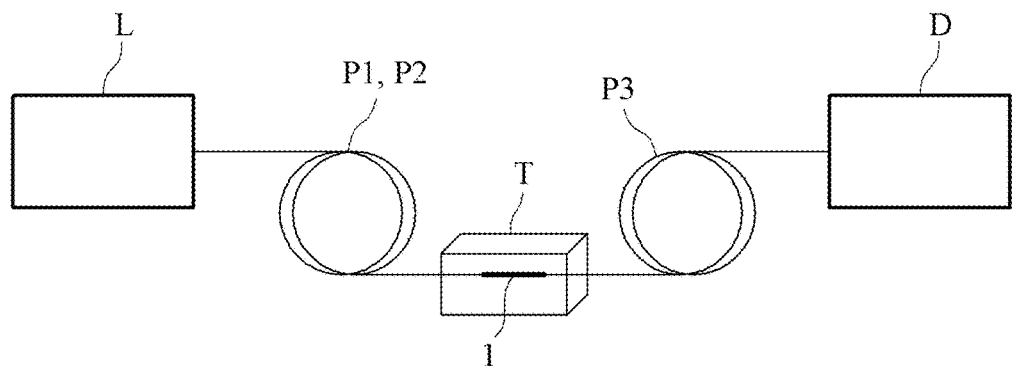
FIG. 17 schematically illustrates a transmission-type sensing system including an optical fiber according to the present disclosure.

For reference, a transmission-type optical sensor that includes the optical fiber 1 of the present disclosure including the optical filter 40 is illustrated in FIG. 17. As illustrated in FIG. 17, light input from the light source L is sensed by a probe including the optical fiber 1 via first and second ports P1 and P2 and then passes through a third port P3, followed by being detected by a detector D. Here, the first port P1 is an input port for guiding input of light, the second port P2 is a sensing port for guiding sensing of light, and the third port P3 is a detection port for guiding detection of light.

Figure 18:
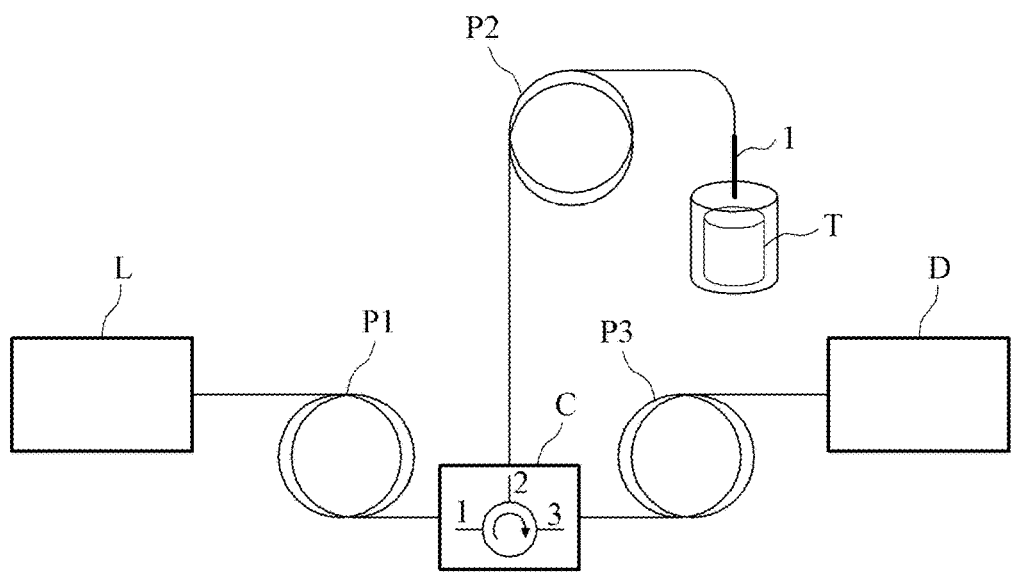
FIG. 18 schematically illustrates a reflective-type sensing system including an optical fiber according to the present disclosure.

In addition, a reflective-type optical sensor that includes the optical fiber 1 including the optical filter 40 is illustrated in FIG. 18. As illustrated in FIG. 18, light, which circulates from the light source L to an input port, a first port P1, via a circulator C, passes through a sensing port, a second port P2, and then is sensed by a probe including the optical fiber 1. The sensed light is reflected by a circulator C and circulated again. Accordingly, the light is detected in the detector D via a detection port, the third port P3.

The optical fiber 1 including the plasmonic optical filter 40 has increased filtering and sensing areas and thus may be applied as a superior optical filter and optical sensor. In addition, the optical fiber 1 may be variously applied even in microenvironments, such as blood vessels, or severe environments requiring long-distance transmission ability, such as geologic storage facilities.

According to the present invention having the aforementioned configuration, first, a plasmonic optical filter is provided at the exposed core of the optical fiber and thus an optical signal generation area increases, which contributes to efficiency increase.

Second, by applying thin-film coating technology limitedly used to flat subjects to be machined while adjusting a rotation axis of an optical fiber, freeform and curved micro devices can be manufactured.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF SYMBOLS

1: OPTICAL FIBER
10: CORE
20: CLADDING
30: JACKET
40: OPTICAL FILTER
50: DEPOSITION APPARATUS
51: CHAMBER
52: GUIDER
53: DRIVING UNIT
54: DEPOSITION UNIT

What is claimed is:

1. An optical fiber, wherein a plasmonic optical filter having a closed curved shape is provided to at least a portion of the optical fiber,
   wherein the plasmonic optical filter is formed by patterning a thin metal film formed into a cylindrical shape at a portion of a circumferential surface of an exposed core with nanopatterns.

2. The optical fiber according to claim 1, wherein the thin metal film is made of at least one of gold, silver, aluminum, and chrome.

3. The optical fiber according to claim 1, wherein the nanopatterns comprise a plurality of holes perforating the thin metal film.

4. The optical fiber according to claim 1, wherein the nanopatterns are arranged side by side.

5. An optical fiber, comprising:
   a core;
   a cladding surrounding a portion of the core and made of a material having a lower refractive index than a material of the core; and
   an optical filter formed into a cylindrical shape at another portion of the core and comprising a thin metal film patterned with nanopatterns.

\* \* \* \* \*